(12) United States Patent
Nakae et al.

(10) Patent No.: US 7,607,339 B2
(45) Date of Patent: Oct. 27, 2009

(54) CERAMIC LAMINATE BODY, GAS SENSOR ELEMENT AND RELATED MANUFACTURING METHOD

(75) Inventors: Makoto Nakae, Nagoya (JP); Shoichiro Emmei, Nagoya (JP); Kiyomi Kobayashi, Kuwana (JP)

(73) Assignee: Denso Corporation, Kariya (JP)

( * ) Notice: Subject to any disclaimer, the term of this patent is extended or adjusted under 35 U.S.C. 154(b) by 234 days.

(21) Appl. No.: 11/706,396

(22) Filed: Feb. 15, 2007

(65) Prior Publication Data

US 2007/0214865 A1     Sep. 20, 2007

(30) Foreign Application Priority Data

Mar. 15, 2006   (JP) .............................. 2006-071077

(51) Int. Cl.
*G01N 27/407*    (2006.01)
(52) U.S. Cl. ..................... 73/31.05; 204/424; 204/429
(58) Field of Classification Search ................ 73/31.05, 73/31.06, 19.01, 23.2; 204/424–429
See application file for complete search history.

(56) References Cited

U.S. PATENT DOCUMENTS 4,657,659 A * 4/1987 Mase et al. ................. 204/410

6,537,431 B1   3/2003 Tatsumoto et al.
2006/0151466 A1* 7/2006 Diehl ..................... 219/448.11

FOREIGN PATENT DOCUMENTS

| DE | 100 23 980 | 1/2001 |
| JP | 09-304321 | 11/1997 |
| JP | 2001-30219 | 2/2001 |
| JP | 2007024670 A * | 2/2007 |

OTHER PUBLICATIONS

German Office Action dated May 13, 2008 (received Sep. 15) issued in counterpart German Application No. 10 2007 011 806.8-44, with English translation.

* cited by examiner

*Primary Examiner*—Harshad Patel
*Assistant Examiner*—Punam Patel
(74) *Attorney, Agent, or Firm*—Nixon & Vanderhye, PC

(57) ABSTRACT

A ceramic laminate body, a gas sensor element employing such a ceramic laminate body and related manufacturing method are disclosed as including first and second ceramic sheets, made of material compositions different from each other, and an intermediate bonding layer, bonding the first and second ceramic sheets to each other so as to form a closed hollow space between the first and second ceramic sheets. The intermediate bonding layer has a multilayer structure including first and second unit intermediate layers laminated on each other such that innermost end portions of the first and second unit intermediate layers are displaced from each other to adapt a difference in degreasing contraction rates of associated component parts.

14 Claims, 11 Drawing Sheets

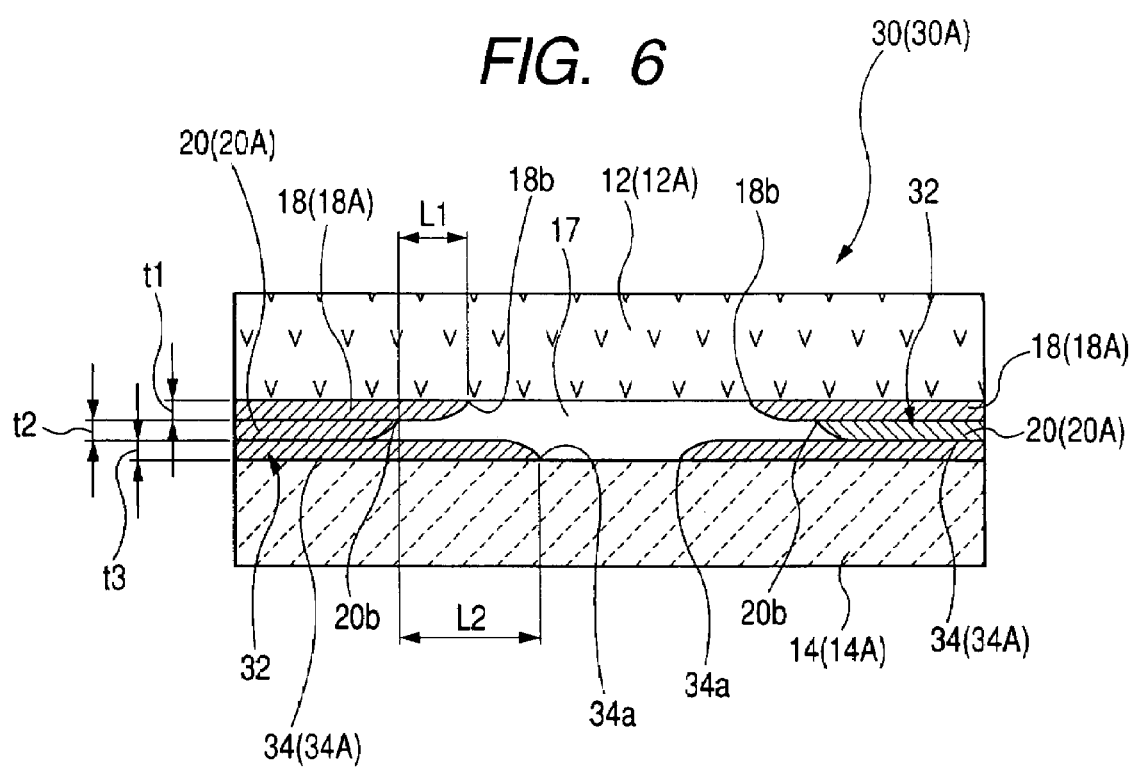
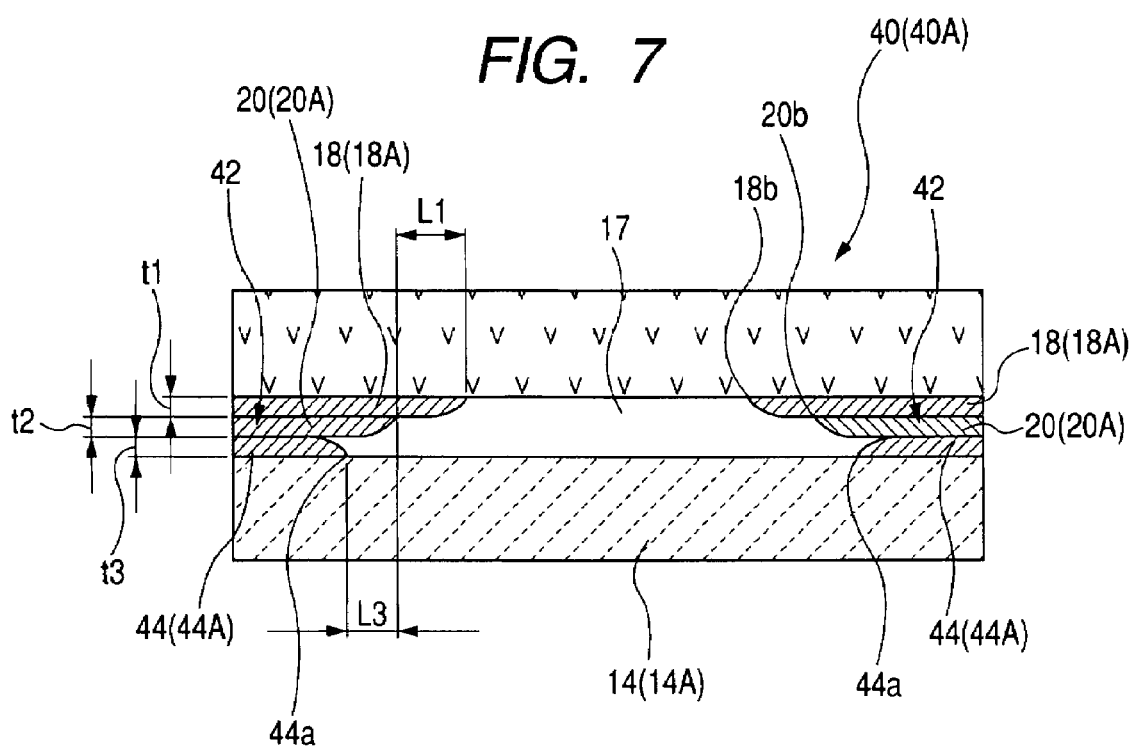

CERAMIC LAMINATE BODY, GAS SENSOR ELEMENT AND RELATED MANUFACTURING METHOD

CROSS REFERENCE TO RELATED APPLICATIONS

This application is based on Japanese Patent Application No. 2006-71077, filed on Mar. 15, 2006, the content of which is hereby incorporated by reference.

BACKGROUND OF THE INVENTION

1. Field of the Invention

The present invention relates to ceramic laminate bodies for use in stack type gas sensor elements and related manufacturing methods and, more particularly, to a ceramic laminate body, composed of a stack of plural ceramic sheets, and a method of manufacturing the ceramic laminate body.

2. Description of the Related Art

Various attempts have heretofore been made to provide laminate type gas sensor elements each of which includes a structure composed of a stack of plural ceramic sheets. The adjacent ceramic sheets are stacked on each other to form a closed hollow space for introducing atmospheric air serving as reference gas or measuring gas.

Such a structure of the ceramic laminate body is disclosed in FIG. 16. As shown in FIG. 16, the ceramic laminate body 110 comprises two ceramic sheets 112, 114 that are stacked on each other via an intermediate bonding layer 116 so as to form a closed hollow space 118 between the two ceramic sheets 112, 114 as disclosed in Japanese Unexamined Patent Application Publication Nos. 9-304321 and 2001-30219.

In manufacturing the ceramic laminate body 110, for instance, an intermediate bonding layer paste is partially coated on one of ceramic green sheets and the other one of the ceramic green sheets is stacked on the one of the ceramic green sheets via the intermediate bonding layer paste, thereby forming an unburned laminate body. Subsequently, the unburned laminate body is fired, thereby obtaining the ceramic laminate body 110 having the closed hollow space 118.

However, during step of firing the unburned laminate body, a stress had occurred in a boundary layer between the ceramic green sheet 112 and the bonding layer paste 116 as shown in FIG. 17, causing a cracking 99 or flaking to occur. This seems to be derived from the fact in that there exists a difference in greasing contraction factor between the ceramic green sheet 114 and the bonding layer paste 116. That is, when firing the unburned laminate body, the unburned laminate body is degreased during temperature rising step. When this takes place, since the bonding layer paste 116 contains a larger amount of binder or solvent than those contained in the ceramic green sheet 114 in normal practice. Therefore, during temperature rising step, a stress occurs in an area between the ceramic green sheet 114 and the bonding layer paste 116 due to a difference in degreasing contraction as shown in FIG. 17, causing a risk to arise with the occurrence of cracking 99 or flaking.

After the ceramic laminate body has reached the maximum temperature during firing step, the ceramic laminate body is subjected to cooling step. During such cooling step, a stress occurs due to a difference in linear coefficients of expansion of the two ceramic green sheets 112A, 114A, causing cracking 99 or flaking to occur at the same time when the temperature rises. That is, one of the two ceramic green sheets 112, 114 is made of alumina in major proportions and the other is made of zirconia in major proportions. In such a case, the two ceramic green sheets 112, 114 have linear coefficients of expansion different from each other. In such a case, the two ceramic green sheets 112, 114 are hardened in different contracting factors during cooling step in a manner as shown in FIG. 18. In FIG. 18, a curve N1 represents a contracting factor of the ceramic green sheet composed of alumina in major proportions and a curve N2 represents a contracting factor of the ceramic green sheet composed of zirconia in major proportions.

With such a difference in contracting factors, a stress occurs in an area between the two ceramic green sheets, causing cracking 99 or flaking to occur in the sheet 114.

SUMMARY OF THE INVENTION

The present has been completed with a view to addressing the above issues and has an object to provide a ceramic laminate body and related manufacturing method that can prevent the occurrence of cracking or flaking.

To achieve the above object, a first aspect of the present invention provides a ceramic laminate body comprising a first ceramic sheet, a second ceramic sheet made of material compositions different from those of the first ceramic sheet, and an intermediate bonding layer, bonding the first and second ceramic sheets to each other so as to form a closed hollow space between the first and second ceramic sheets. The intermediate bonding layer has a multilayer structure including first and second unit intermediate layers laminated on each other such that an innermost end portion of one of the first and second unit intermediate layers protrudes inward in the closed hollow space and is displaced from an innermost end portion of the other of the first and second unit intermediate layers.

With such a structure of the ceramic laminate body, the intermediate bonding layer has the multilayer structure including the unit intermediate layers formed in more than two layers. In addition, at least one set of unit intermediate layers are stacked on each other under a status where the innermost end portions are displaced from each other. This results in capability of preventing cracking or flaking from occurring in the ceramic sheets during firing step in the course of manufacturing the ceramic laminate body.

That is, during firing step, the temperature of the ceramic laminate body rises during which the ceramic sheets and the intermediate bonding layer are degreased and contracted. When this takes place, due to a difference in degreasing contraction factors, a stress occurs on a boundary area between the ceramic sheets and the intermediate bonding layer.

Further, since the two ceramic sheets have different material compositions, a contraction difference occurs between the two ceramic sheets due to a difference in thermal expansion coefficients caused in both materials during step of cooling the ceramic laminate body in the course of firing step. This causes a stress to occur between the two ceramic sheets via the intermediate bonding layer even in cooling step.

These stresses concentrate particularly at a bonding boundary portion at an area close proximity to the innermost end portion of the intermediate bonding layer.

However, with the laminate structure of the present embodiment implementing the present invention, the presence of the multilayer structure forming the intermediate bonding layer allows at least the adjacent unit intermediate layers to be stacked on each other with the innermost end portions being displaced from each other. This allows the stresses to be dispersed, making it possible to prevent cracking or flaking from taking place in the ceramic sheets.

As set forth above, the present invention makes it possible to provide a ceramic laminate body and related manufacturing method that can prevent the occurrence of cracking or flaking of component parts.

A second aspect of the present invention provides a gas sensor element comprising a ceramic laminate body including a first ceramic sheet, a second ceramic sheet made of material compositions different from those of the first ceramic sheet, and an intermediate bonding layer, bonding the first and second ceramic sheets to each other so as to form a closed hollow space between the first and second ceramic sheets, which has a multilayer structure including first and second unit intermediate layers laminated on each other such that an innermost end portion of one of the first and second unit intermediate layers protrudes inward in the closed hollow space and is displaced from an innermost end portion of the other of the first and second unit intermediate layers. A reference gas detecting electrode is formed on one surface of the first ceramic sheet in face-to-face relation with the closed hollow space. A measuring gas detecting electrode is formed on the other surface of the first ceramic sheet and exposed in a measuring gas chamber. A diffusion resistance layer is stacked on the other surface of the first ceramic sheet so as to define the measuring gas chamber in an area around the measuring gas detecting electrode and operative to permeate measuring gas to the measuring gas chamber. A shielding layer is laminated on the diffusion resistance layer.

With such a structure of the gas sensor element employing the ceramic laminate body, stresses acting on the ceramic sheets can be alleviated due to the presence of the multilayer structure of the intermediate bonding layer placed between the adjacent ceramic sheets during cooling step after completion of firing step. Thus, neither cracking nor flaking occurs in the ceramic sheets during cooling step of the ceramic laminate body. This allows the gas sensor element to have a long operating life with an increase in reliability of operation.

A third aspect of the present invention provides a method of manufacturing a ceramic laminate body, the method comprising the steps of preparing a first green ceramic sheet, preparing a second green ceramic sheet made of material compositions different from those of the first ceramic sheet, forming first and second bonding layer pastes, having different degreasing contraction factors, on at least one of the first and second ceramic sheets to form an intermediate bonding layer in a multilayer structure, stacking the first and second ceramic green sheets via the intermediate bonding layer so as to form a closed hollow space for thereby providing an unburned laminate body, and firing the unburned laminate body to form the ceramic laminate body.

In manufacturing the ceramic laminate body, the first and second bonding layer pastes are formed on at least one of the first and second ceramic green sheets to form the intermediate bonding layer in the multilayer structure, with the first and second bonding layer pastes having the degreasing contraction factors different from each other. This allows firing step to be carried out under a condition where neither cracking nor flaking occurs in the ceramic green sheets.

That is, during firing step of the ceramic laminate body, the ceramic green sheets and the intermediate bonding layer are degreased and contracted at different rates in a process of rising temperatures of the ceramic laminate body during firing step. When this takes place, due to a difference in degreasing contraction factors, stresses occur in boundary areas between the ceramic green sheets and the intermediate bonding layer.

Such stresses concentrate particularly on the bonding boundary portion in the vicinity of the innermost end portions of the bonding layer pastes. These stresses cause cracking or flaking to take place in the ceramic green sheet.

With the manufacturing method according to the present invention, however, the bonding layer pastes are formed in the multilayer structure and, among the bonding layer pastes formed in plural layers, at least one set of adjacent bonding layer pastes have the different degreasing contraction factors. This allows stresses to occur in the adjacent bonding layer pastes having the different degreasing contraction factors so as to cause the dispersion of the stresses, thereby preventing the ceramic green sheets from damages such as cracking or flaking.

For instance, the bonding layer paste closer to the ceramic green sheet is selected to have the degreasing contraction factor closer to that of the ceramic green sheet than that of the other bonding layer paste remote from the relevant ceramic green sheet, enabling the stresses to be effectively alleviated.

In such a way, the stresses resulting from the difference in the degreasing contraction factors of the ceramic green sheets and the bonding layer pastes can be efficiently dispersed, making it possible to prevent the ceramic green sheets from cracking or flaking.

As set forth above, according to the third aspect of the present invention, it becomes possible to provide a ceramic laminate body and related manufacturing method that can prevent ceramic green sheets from cracking or flaking.

BRIEF DESCRIPTION OF THE DRAWINGS

FIG. 6 is a cross sectional view showing a ceramic laminate body of a second embodiment according to the present invention.

FIG. 7 is a cross sectional view showing a ceramic laminate body of a third embodiment according to the present invention.

DETAILED DESCRIPTION OF THE PREFERRED EMBODIMENTS

Figure 1:
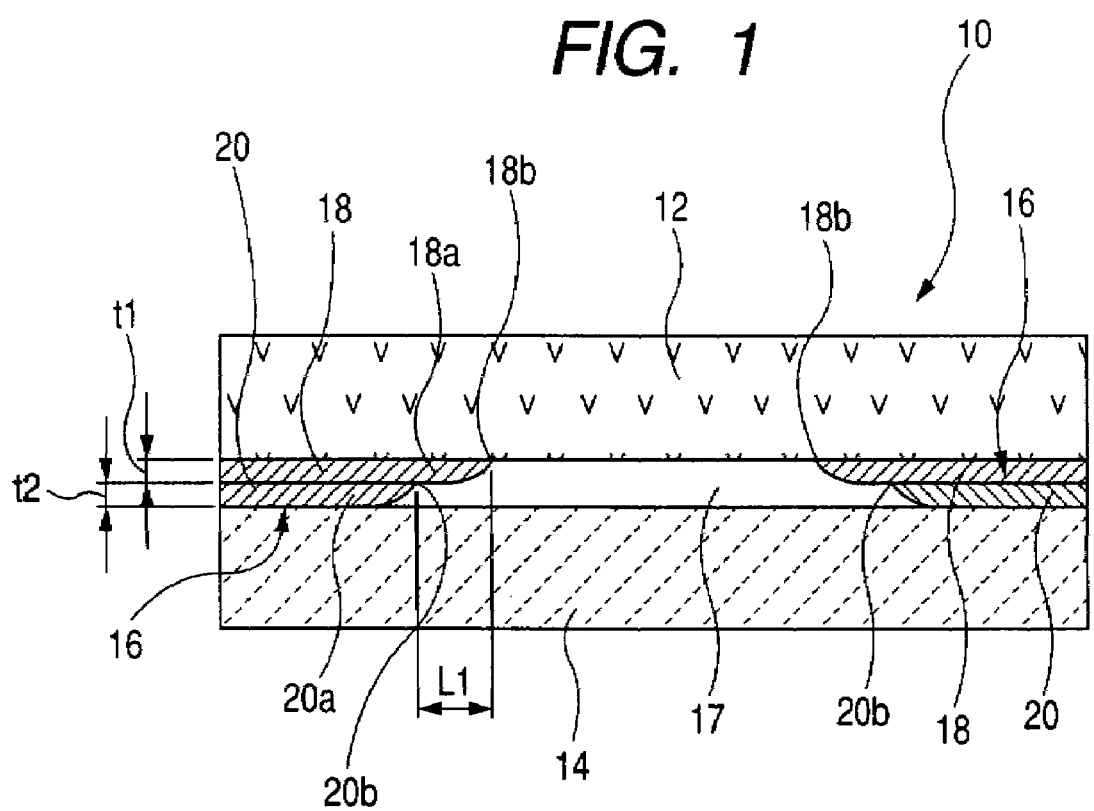
FIG. 1 is a cross sectional view showing a ceramic laminate body of a first embodiment according to the present invention.

Now, laminate ceramic bodies, gas sensor elements of various embodiments and related manufacturing methods according to the present invention are described below in detail with reference to the accompanying drawings. However, the present invention is construed not to be limited to such embodiments described below and technical concepts of the present invention may be implemented in combination with other known technologies or the other technology having functions equivalent to such known technologies.

In the following description, like reference characters designate like or corresponding parts throughout the several views. Also in the following description, description on the same component parts of one embodiment as those of another embodiment is omitted, but it will be appreciated that like reference numerals designate the same component parts throughout the drawings.

First Embodiment

Now, a ceramic laminate body and related manufacturing method of a first embodiment according to the present invention are described below in detail with reference to FIGS. 1 to 5.

A ceramic laminate body 10 comprises two ceramic sheets 12, 14, composed of materials different from each other, an intermediate bonding layer 16 interposed between the two ceramic sheets 12, 14 in an area around outer circumferential peripheries of the two ceramic sheets 12, 14, and a closed hollow space 17 serving as a hollow section and defined between the two ceramic sheets 12, 14 in an area inside the intermediate bonding layer 16.

The intermediate bonding layer 16 takes the form of a multilayer structure composed of unit intermediate layers 18, 20 laminated in two layers. The unit intermediate layer 18 has an inward end portion 18a whose innermost end 18b exposed to the hollow section 17. Likewise, the unit intermediate layer 20 has an inward end portion 20a whose innermost end 20b exposed to the hollow section 17 at an area outward of the inward end portion 18a of the unit intermediate layer 18. That is, the inward end portions 18a, 20a of the first and second unit intermediate layers 18, 20 are horizontally dislocated from each other by a given distance.

With the ceramic laminated structure 10 shown in FIG. 1, the unit intermediate layers 18, 20 have thickness t1, t2, respectively, each of which lies in a value ranging from 5 to 100 μm.

Further, the innermost end portions 18b, 20b of the unit intermediate layers 18, 20 are displaced from each other by a distance L1 that is selected to be greater than the thickness t1 of the unit intermediate layer 18.

Further, of the two ceramic sheets 12, 14, one ceramic sheet 12 is made of zirconia in major proportions and the other ceramic sheet 14 is made of alumina in major proportions.

Furthermore, the hollow section 17 is defined between the two ceramic sheets 12, 14 in a substantially squared shape as viewed in plan view and placed in an area such that the hollow section 17 is surrounded in four or three directions.

Moreover, the innermost end portions 18b, 20b of the unit intermediate layers 18, 20, forming the intermediate bonding layer 16, are gently formed in substantially circular arc shapes in cross section, respectively. The innermost end portion 18b of the unit intermediate layer 18, formed on the ceramic sheet 12, has a distal end formed in a substantially circular arc shape placed on a surface of the ceramic sheet 12. In addition, the innermost end portion 20b of the unit intermediate layer 20, formed on the ceramic sheet 14, has a distal end formed in a substantially circular arc shape placed on a laminate surface of the unit intermediate layer 18.

Figure 2:
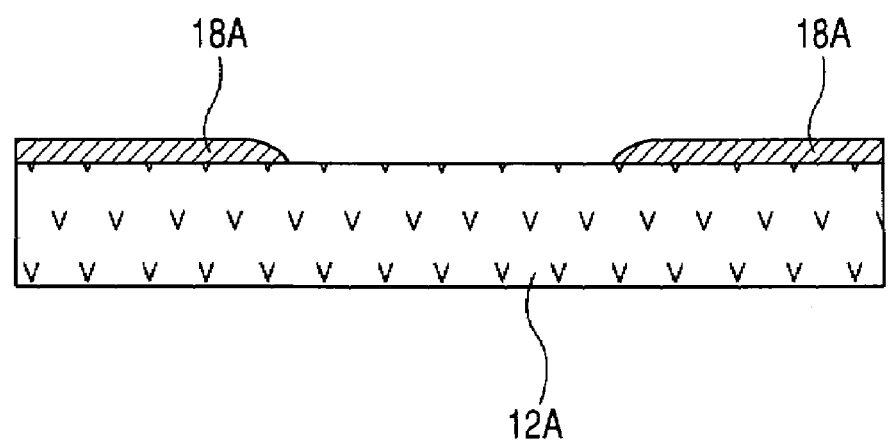
FIG. 2 is a cross sectional view showing a ceramic green sheet, used for the ceramic laminate body shown in FIG. 1, with a status in which a first bonding layer ceramic paste is applied.

In manufacturing the ceramic laminate body 10 of the present embodiment, in first step, a first ceramic green sheet 12A, having one surface applied with a first bonding paste 18A as shown in FIG. 2. In next step, a second bonding paste 20A is applied onto a laminate surface of the first bonding paste 18A applied onto the first ceramic green sheet 12A as shown in FIG. 3.

Figure 4:
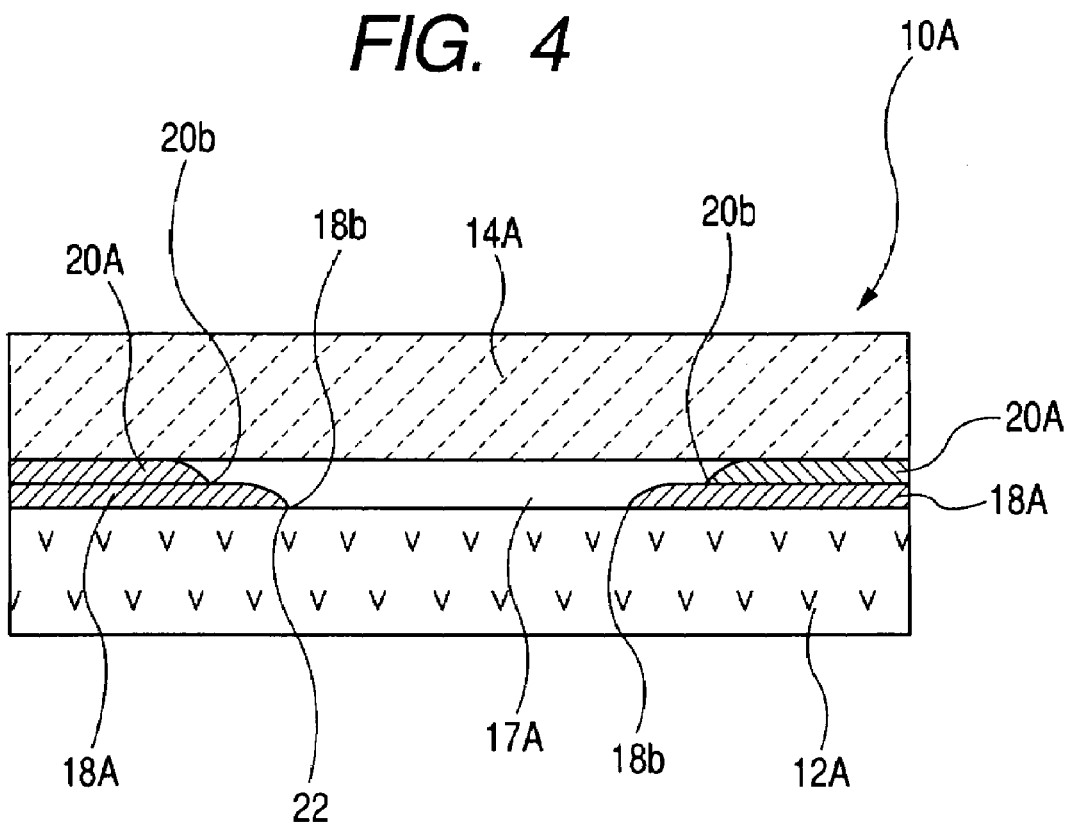
FIG. 4 is a cross sectional view showing an unburned ceramic laminate body, employing the ceramic sheet shown in FIG. 3, for use in manufacturing the ceramic laminate body of the first embodiment shown in FIG. 1.

In subsequent step shown in FIG. 4, a second ceramic green sheet 14A is stacked on the first ceramic green sheet 12A via the first and second bonding layer pastes 18A, 20A, laminated in plural layers, to form an unburned laminate body 10A. Thereafter, the unburned laminate body 10A is subjected to ceramic firing. When this takes place, the first and second bonding layer pastes 18A, 20A formed in plural layers have degreasing contraction rates that are different from each other.

Figure 3:
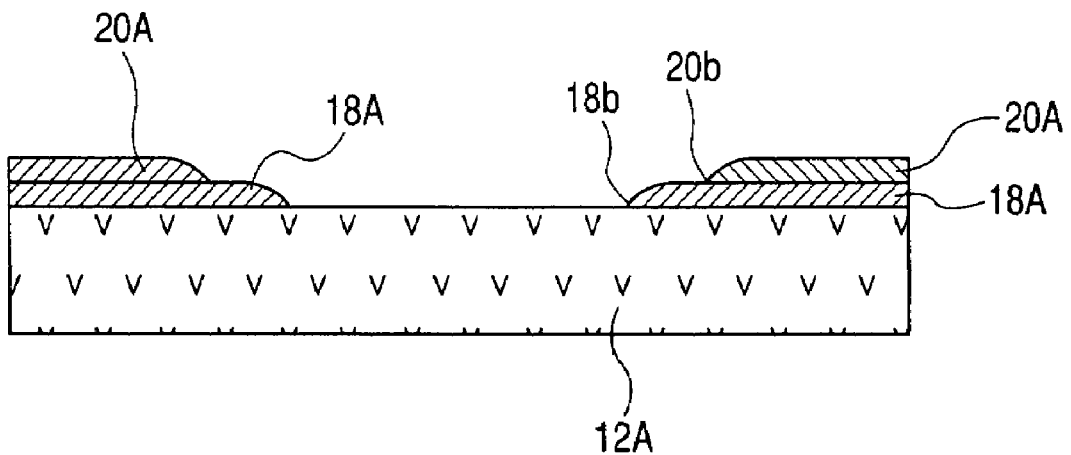
FIG. 3 is a cross sectional view showing the ceramic green sheet, used for the ceramic laminate body shown in FIG. 1, with a status in which a second bonding layer paste is formed on the first bonding layer ceramic paste.

Hereunder, description is made of a basic sequence of steps of performing a method of manufacturing the ceramic laminate body 10 of the present embodiment with reference to FIGS. 2 to 4.

First, as shown in FIG. 2, the first ceramic green sheet 12A, made of zirconia in major proportions, is prepared and the bonding paste 18A is coated on the one surface of the ceramic green sheet 12A. During such step, the first bonding paste 18A is coated in a circumferential area except for a space in which the hollow section 17 is formed on a final stage as shown in FIG. 1. The bonding paste 18A is composed of a paste containing alumina ceramic particles and has a less amount of binders than those contained in the bonding paste 20A, described below in detail, and a low degreasing contraction rate.

Figure 5:
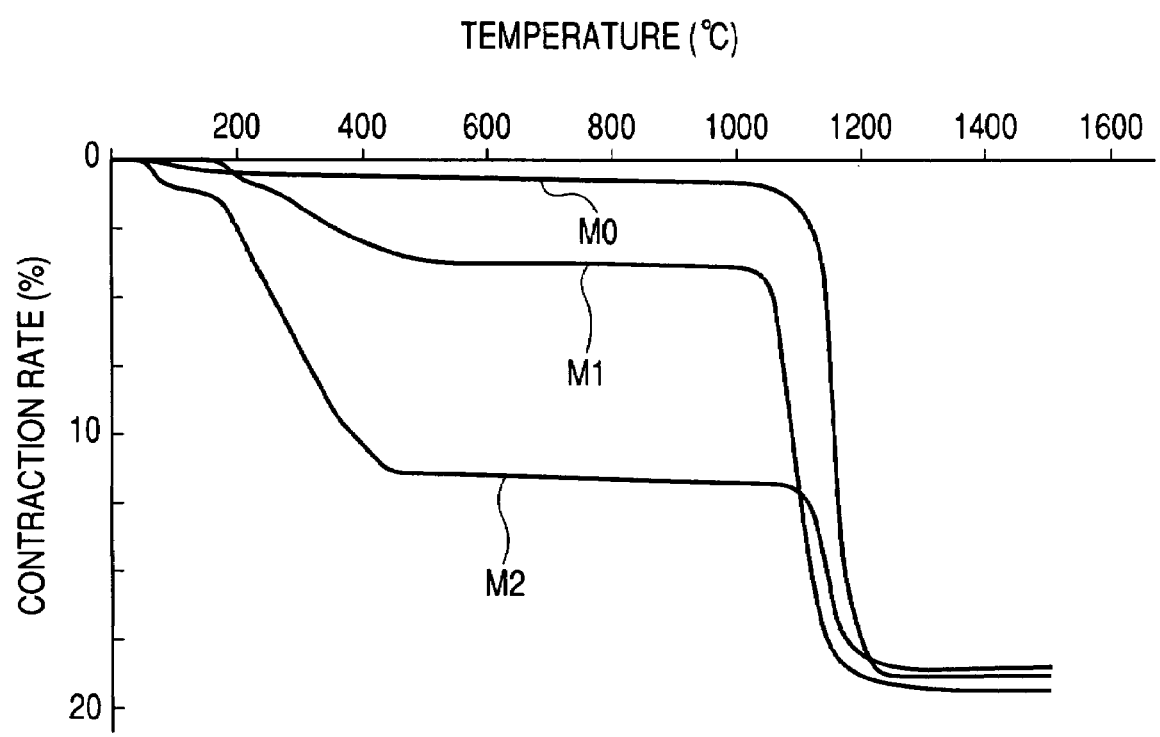
FIG. 5 is a graph showing variations in degreasing contraction factors of the ceramic green sheet and the first and second bonding layer pastes in term of temperatures in the ceramic laminate body of the first embodiment shown in FIG. 1.

That is, as shown in FIG. 5, the bonding paste 18A has an intermediate degreasing contraction rate between the bonding paste 20A and those of the ceramic green sheet 12A, 14A. In FIG. 5, curves M0, M1, M2 represent degreasing contraction rates of the ceramic green sheet 12A, the bonding paste 18A and the bonding paste 20A, respectively. In addition, under a status where the green ceramic sheets 12A, 14A and the intermediate bonding layer lay at temperatures up to approximately 1000° C., these component elements remain under degreasing contraction regions at which contraction rates are referred to as the "degreasing contraction rates".

After coating step has been completed, the first bonding paste 18A is dried.

Then, as shown in FIG. 3, the second bonding paste 20A is coated on a surface of the first bonding paste 18A that has been already dried. During such coating step, the second bonding paste 20A is coated on the surface of the first bonding paste 18A such that the innermost end 20b of the second bonding paste 20A is remote outward from the innermost end 18b of the first bonding paste 18A. In addition, the second bonding paste 20A is composed of a bonding paste, containing alumina ceramic particles with a higher binder content than that of the first bonding paste 18A, which has a high bonding capability.

After coating step has been completed, the second bonding paste 20A is dried.

In next step, as shown in FIG. 4, the second ceramic green sheet 14A, including alumina particles in major proportions, is stacked onto the second bonding paste 20A and then pressed against the first ceramic green sheet 12A. This results in the formation of the unburned laminate body 10A with the hollow section 17A being defined.

In subsequent step, the unburned laminate body 10A is fired, thereby obtaining the ceramic laminate body 1 as shown in FIG. 1. During such firing step, the unburned laminate body 10A is placed in a furnace and heated to the maximum temperature of 1500° C., after which the unburned laminate body 10A is gradually cooled to a normal temperature.

Moreover, upon completion of firing step, the first and second green sheets 12A, 14A become the ceramic sheets 12, 14, respectively, and the first and second bonding layer pastes 18A, 20A become the unit intermediate layers 18, 20, respectively.

Now, the operation and advantageous effects of the ceramic laminate body 10 of the present embodiment are described below.

The intermediate bonding layer 16 takes the form of a multilayer structure including the unit intermediate layers 18, 20 formed in two layers, with the unit intermediate layers 18, 20 being laminated under a status where the respective innermost ends 18b, 20b are displaced from each other. This prevents cracking or flaking from taking pace in the ceramic sheets 12, 14 (the first and second green sheets 12A, 14A) during firing step conducted when manufacturing the ceramic laminate body 10.

That is, during firing step, the temperature of the ceramic laminate body 10 (the unburned laminate body 10A) is raised, during which degreasing contractions occur in the ceramic sheets 12, 14 (the first and second ceramic green sheets 12A, 14A) and the intermediate bonding layer 16 (the first and second bonding layer pastes 18A, 20A). When this takes place, due to a difference in degreasing contraction rates, stress occurs on a boundary area between the ceramic sheets 12, 14 (the first and second ceramic green sheets 12A, 14A) and the intermediate bonding layer 16 (the first and second bonding layer pastes 18A, 20A).

Further, since the ceramic sheets 12, 14 (the first and second ceramic green sheets 12A, 14A) have material compositions different from each other, a probability occurs for a differential shrinkage to occur due to a difference in thermal expansion coefficients of materials forming the ceramic sheets 12, 14 during step of cooling the ceramic laminate body 10 in the course of firing step. This causes a probability to take place in which stress occurs in the two ceramic sheets 12, 14 (the first and second ceramic green sheets 12A, 14A) via the intermediate bonding layer 16 (the first and second bonding layer pastes 18A, 20A).

These stresses concentrate on a joint boundary area 22 in the vicinity of the innermost end portions 18b, 20b. These stresses result in causes for cracking or flaking to take place in the ceramic sheets.

In contrast to such issues, with the ceramic laminate body 10 of the present embodiment according to the present invention, the intermediate bonding layer 16 (the first and second bonding layer pastes 18A, 20A) has the multilayer structure, as set forth above, and at least adjacent first and second bonding layer pastes 18A, 20A are placed under a condition in which respective innermost ends 18b, 20b are displaced from each other. This allows stresses to be dispersed, thereby making it possible to prevent the occurrence of cracking or flaking of the two ceramic sheets 12, 14 (the first and second ceramic green sheets 12A, 14A).

Further, the first and second bonding layer pastes 18A, 20A formed in two layers have the degreasing contraction rates that are different from each other. Even with such a difference in the degreasing contraction rates, cracking or flaking can be effectively prevented from occurring in the first and second ceramic green sheets 12A, 14A in the course of firing step.

That is, as set forth above, cracking or flaking occurs in the ceramic laminate body due to a difference in degreasing contraction rates of the first and second ceramic green sheets 12A, 14A and the first and second bonding layer pastes 18A, 20A. Such an issue can be addressed with the ceramic laminate body 10 due to the presence of the first and second bonding layer pastes 18A, 20A having different degreasing contraction rates. Such a difference in degreasing contraction rates causes stresses to occur in the first and second bonding layer pastes 18A, 20A in dispersed patterns, enabling the prevention of cracking or flaking of the first and second ceramic green sheets 12A, 14A.

Further, the unit intermediate layers 18, 20, forming the intermediate bonding layer 16, are formed in thickness ranging from 5 to 100 μm. This allows stresses to be adequately dispersed.

Furthermore, the innermost ends 18b, 20b of the unit intermediate layers 18, 20 are displaced from each other by a distance L1 selected to be greater than thickness t1 of the unit intermediate layer 18 whose innermost end 18b protrudes further inward from the innermost end 20b of the unit intermediate layer 20. This enables stresses, occurring in the ceramic sheets during firing step, to be adequately dispersed, thereby effectively preventing the occurrence of cracking or flaking in the unit intermediate layers 18, 20.

Moreover, the first bonding layer paste 18A is composed of adhesive paste and the second bonding layer paste 20A is composed of ceramic paste having a degreasing contraction rate falling in an intermediate value between that of the adhesive paste (the first bonding layer paste 18A) and those of the first and second ceramic green sheets 12A, 14A. This allows the ceramic paste (the second bonding layer paste 20A) to alleviate stress, while permitting the adhesive paste (first bonding layer paste 18A) to easily bond the first and second ceramic green sheets 12A, 14A to each other. Therefore, it becomes possible to easily manufacture the ceramic laminate body 10 under a state effective for preventing the occurrence of cracking or flaking in the ceramic sheets 12A, 14A.

As set forth above, the present invention makes it possible to provide a ceramic laminate body, capable of preventing the occurrence of cracking or flaking, and a method of manufacturing such a ceramic laminate body.

Second Embodiment

A ceramic laminate body of a second embodiment according to the present invention is described with reference to FIG. 6.

In FIG. 6, reference numerals in parentheses represent component parts of an unburned ceramic laminate body 30A.

As shown in FIG. 6, the ceramic laminate body 30 of the present embodiment comprises the first and second ceramic sheets 12, 14 that are bonded to each other through an intermediate bonding layer 32 formed in a triple-layer structure composed of the first and second unit intermediate layers 18, 20 and an additional unit intermediate layer 34.

Among the unit intermediate layers 18, 20, 34 formed in the triple layers, the unit intermediate layers 18, 20 act in the same ways as the unit intermediate layers 18, 20 of the ceramic laminate body 10 of the first embodiment mentioned above.

With the ceramic laminate body 30 of the second embodiment, the third unit intermediate layer 34 is interposed between the second unit intermediate layer 20 and the second ceramic sheet 14. The unit intermediate layer 34 has the innermost end 34a located further inward from those of the first and second unit intermediate layers 18, 20.

More particularly, the innermost end 34a of the third unit intermediate layer 34 is displaced from the innermost end 20b of the second unit intermediate layer 20 by a distance L2, selected to be greater than thickness t3 of the third unit intermediate layer 34, which is greater than the distance L1 by which the innermost end 18b of the first unit intermediate layer 18 is dislocated from the innermost end 20b of the second unit intermediate layer 20. In addition, the thickness t3 of the third unit intermediate layer 34 lies in a value ranging from 5 to 100 μm.

In manufacturing the ceramic laminate body 30, first and second bonding layer pastes 18A, 20A, forming the unit intermediate layers 18, 20, are coated on a ceramic green sheet 12A in sequence to form the ceramic green sheet 12A in the same manner as conducted in manufacturing the ceramic laminate body 10 of the first embodiment shown in FIG. 1.

Meanwhile, a third bonding layer paste 34A is coated on a second ceramic green sheet 14A that forms the second ceramic sheet 14 in subsequent stage. The third bonding paste 34A has a degreasing contraction rate, nearly equal to the first bonding layer paste 18A, which has a value appearing between that of the second bonding layer paste 20A and those of the ceramic green sheets 12A, 14A.

Subsequently, the two ceramic green sheets 12A, 14A are stacked on each other so as to overlap the bonding layer pastes 24A, 34A.

Upon stacking the two ceramic green sheets 12A, 14A in a manner mentioned above, the bonding layer pastes 18A, 34A, closer to the ceramic green sheets 12A, 14A, are made to have the degreasing contraction rates closer to those of the ceramic green sheets 12A, 14A.

The method of manufacturing the ceramic laminate body 30 of the second embodiment is conducted in other same steps as those of the manufacturing method of the first embodiment and, hence, redundant description is herein omitted for the sake of simplicity.

With the ceramic laminate body 30 of the present embodiment, since the intermediate bonding layer 32 is comprised of the unit intermediate layers 18, 20 and 34 formed in the triple layers, stresses acting on these component elements can be dispersed in a further efficiently distributed pattern.

The bonding layer pastes 18A, 34A, closer to the ceramic green sheets 12A, 14A, are selected to have the degreasing contraction rates closer to those of the ceramic green sheets 12A, 14A and remote from that of the bonding layer paste 20A that is remote from the ceramic green sheets 12A, 14A. This results in capability of effectively alleviating stresses acting on the bonding layer pastes.

The ceramic laminate body 30 of the present embodiment has the other advantageous effects as those of the ceramic laminate body 10 of the first embodiment.

Third Embodiment

A ceramic laminate body of a third embodiment according to the present invention is described with reference to FIG. 7.

In FIG. 7, reference numerals in parentheses represent component parts of an unburned ceramic laminate body 40A.

As shown in FIG. 7, the ceramic laminate body 40 of the present embodiment comprises the first and second ceramic sheets 12, 14 that are bonded to each other through an intermediate bonding layer 42 formed in a triple layer composed of the first and second unit intermediate layers 18, 20 and an additional unit intermediate layer 44.

Among the unit intermediate layers 18, 20, 44 formed in the triple layers, the first and second ceramic sheets 12, 14 correspond to the first and second ceramic sheets 12, 14, forming the intermediate bonding layer 16 of the ceramic laminate body 10 of the first embodiment shown in FIG. 1, respectively.

With the ceramic laminate body 40 of the third embodiment, the third unit intermediate layer 44 is interposed between the second unit intermediate layer 20 and the second ceramic sheet 14. The unit intermediate layer 44 has the innermost end 44a located further outward from the innermost end 20b of the second unit intermediate layer 20.

More particularly, the innermost end 44a of the unit intermediate layer 44 is displaced from the innermost end 20b of the second unit intermediate layer 20 by a distance L3, selected to be greater than thickness t3 of the third unit intermediate layer 44.

In manufacturing the ceramic laminate body 40, first and second bonding layer pastes 18A, 20A, forming the unit intermediate layers 18, 20, are coated on a ceramic green sheet 12A in sequence to form the ceramic sheet 12A in the same manner as conducted in manufacturing the ceramic laminate body 10 of the first embodiment shown in FIG. 1.

Meanwhile, a third bonding layer paste 44A is coated on a second ceramic green sheet 14A that forms the second ceramic sheet 14. The third bonding layer paste 44A has a degreasing contraction rate, nearly equal to the first bonding layer paste 18A, which has a value appearing between that of the second bonding paste layer 20A and those of the ceramic green sheets 12A, 14A.

Subsequently, the two ceramic green sheets 12A, 14A are stacked on each other so as to overlap the bonding layer pastes 24A, 34A.

Upon stacking the two ceramic green sheets 12A, 14A in a manner mentioned above, the bonding layer pastes 18A, 34A, closer to the ceramic green sheets 12A, 14A, are made to have the degreasing contraction rates closer to those of the ceramic green sheets 12A, 14A.

The method of manufacturing the ceramic laminate body 40 of the second embodiment is conducted in the same other steps as those of the manufacturing method of the first embodiment.

The ceramic laminate body 40 of the present embodiment has the other advantageous effects as those of the ceramic laminate body 10 of the first embodiment.

Fourth Embodiment

A ceramic laminate body of a fourth embodiment according to the present invention is described with reference to FIG. 8.

Figure 8:
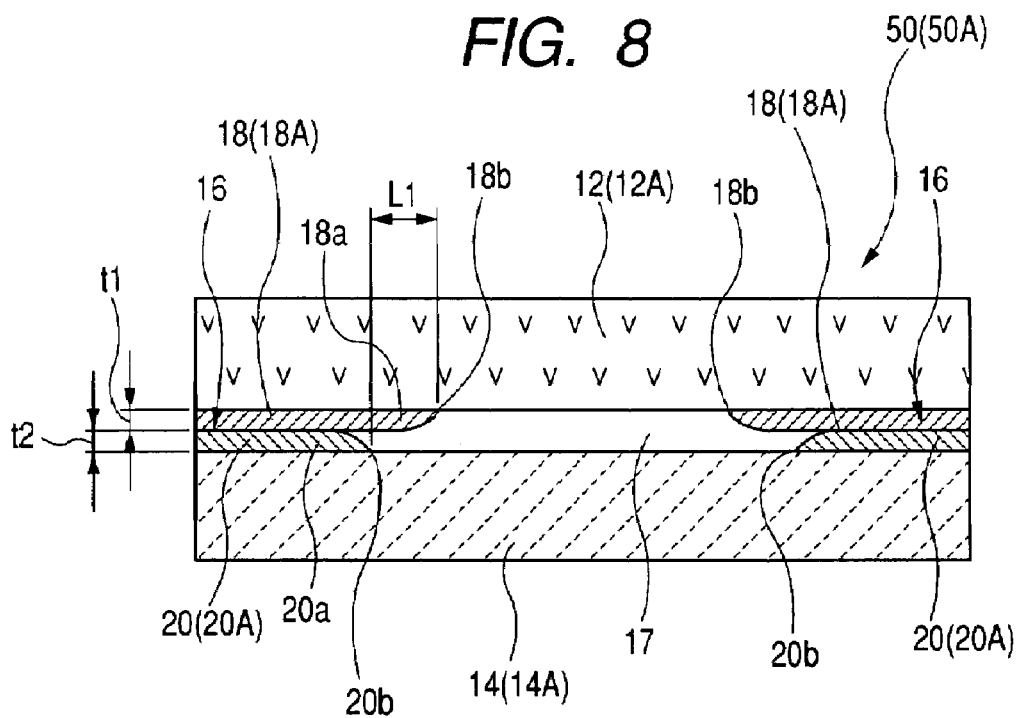
FIG. 8 is a cross sectional view showing a ceramic laminate body of a fourth embodiment according to the present invention.

In FIG. 8, reference numerals in parentheses represent component parts of an unburned ceramic laminate body 30A.

The ceramic laminate body 50 of the present embodiment differs from the ceramic laminate body 10 of the first embodiment in that the unit intermediate layer 20 has the inward end portion 20a formed in a substantially arc shape in cross section that is oriented in opposite direction to the inward end portion 20a of the second unit intermediate layer 20 forming the ceramic laminate body 10 of the first embodiment.

That is, the inward end portions 18a, 20a of both the two unit intermediate layers 18, 20 are placed in face-to-face relation with respect to each other.

In manufacturing the ceramic laminate body 50, the first bonding layer paste 18A is coated on the first ceramic green sheet 12A and the second bonding layer paste 20A is coated on the second ceramic green sheet 20A. Subsequently, the two ceramic green sheets 12, 14 are laminated on each other so as to overlap the first bonding layer paste 18A and the second bonding layer paste 20A.

The ceramic laminate body 50 of the present embodiment has the same other structure as that of the ceramic laminate body 10 of the first embodiment and has similar advantageous effects.

Fifth Embodiment

A ceramic laminate body of a fifth embodiment according to the present invention is described with reference to FIG. 9.

Figure 9:
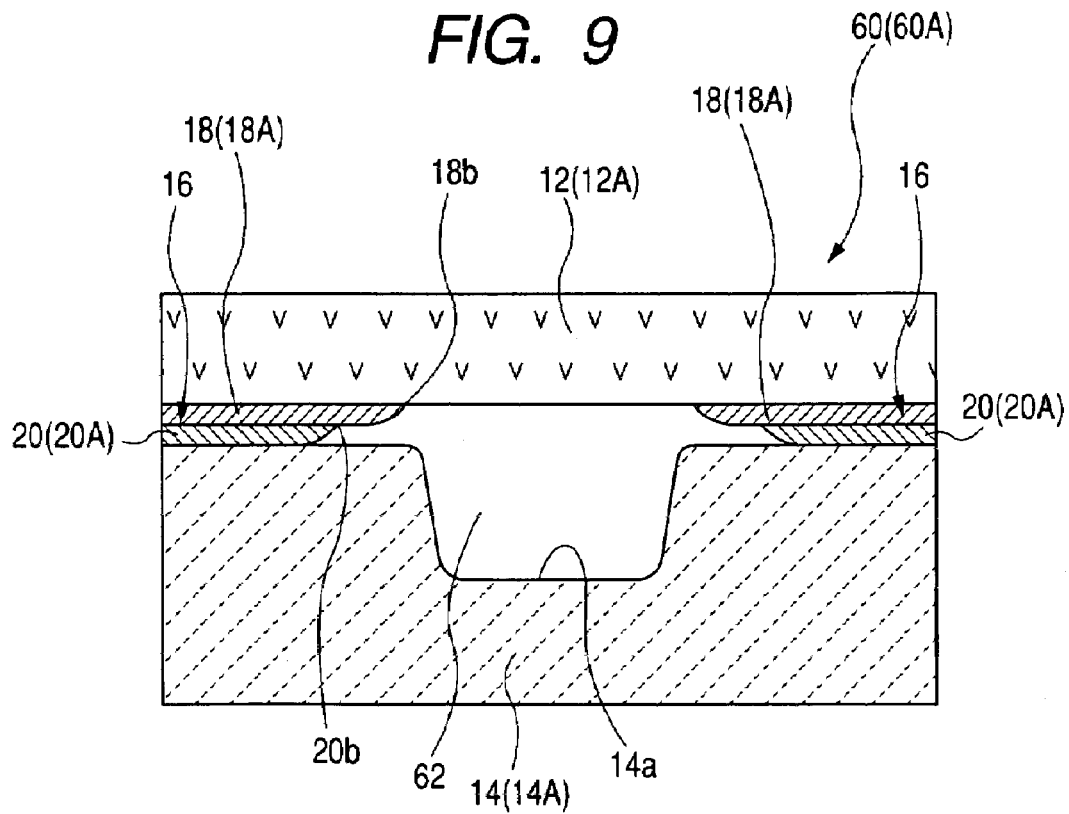
FIG. 9 is a cross sectional view showing a ceramic laminate body of a fifth embodiment according to the present invention.

In FIG. 9, reference numerals in parentheses represent component parts of an unburned ceramic laminate body 60A.

The ceramic laminate body 60 of the present embodiment differs from the ceramic laminate body 10 of the first embodiment in that the second ceramic sheet 14 is formed with a recessed portion 14a to provide a hollow section 62 in an increased volume.

That is, the recessed portion 14a is formed in the second ceramic sheet 14 on a surface thereof facing the intermediate bonding layer 16 at a central area inward of the intermediate bonding layer 16.

The recessed portion 14a may be formed in the second green ceramic sheet 14A by cutting or press forming.

The ceramic laminate body 60 of the present embodiment has the same other structure as that of the ceramic laminate body 10 of the first embodiment and has similar advantageous effects.

Sixth Embodiment

A ceramic laminate body of a sixth embodiment according to the present invention is applied to a gas sensor element, which is described with reference to FIG. 10.

Figure 10:
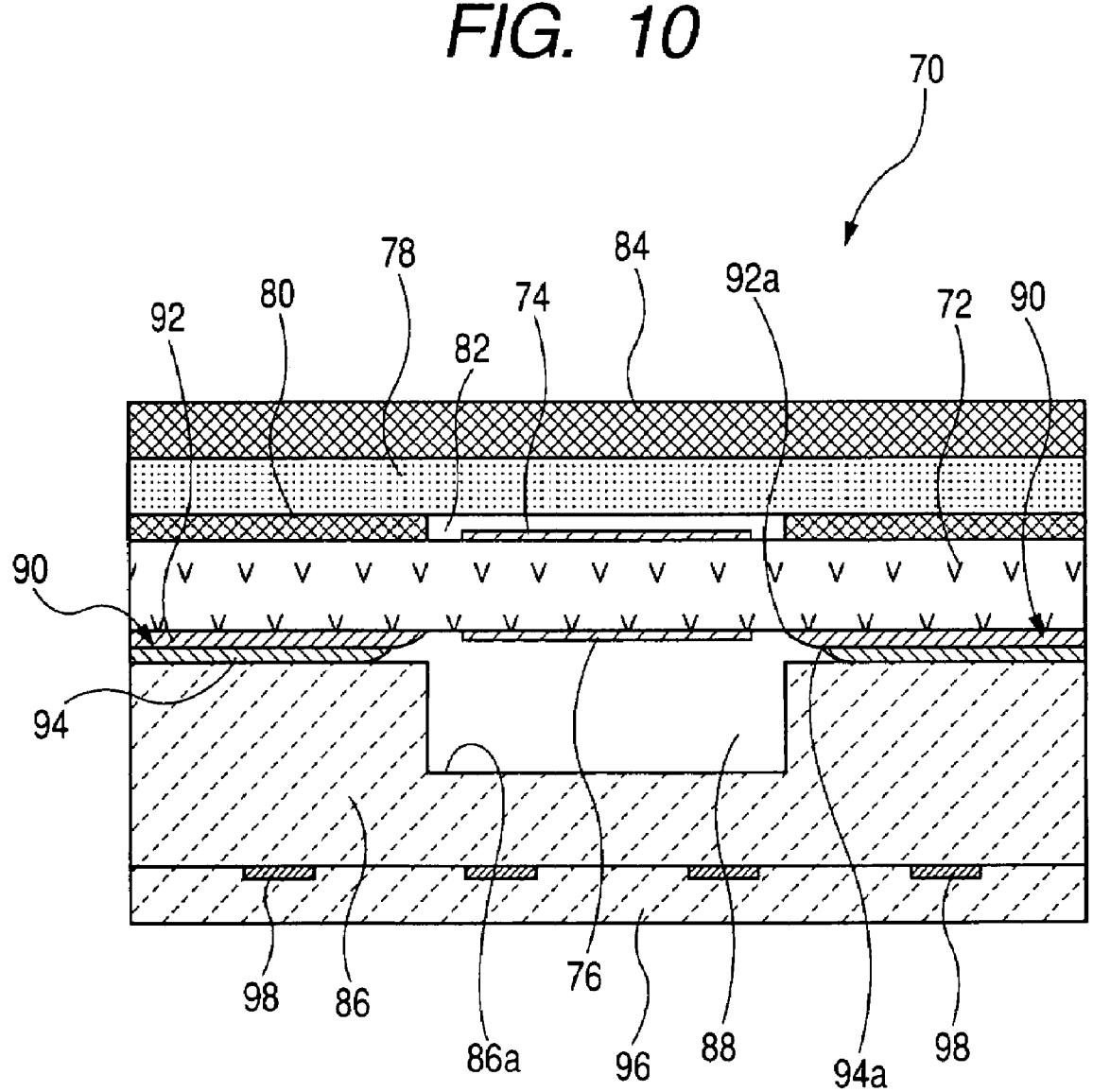
FIG. 10 is a cross sectional view showing a gas sensor element of a sixth embodiment according to the present invention.

As shown in FIG. 10, the gas sensor element 70 comprises a solid electrolyte body 72, having oxygen ion conductivity, which has one surface formed with a measuring gas detecting electrode 74 and the other surface formed with a reference gas detecting electrode 76. Further, the gas sensor element 70 comprises a diffusion resistance layer 78, placed on the solid electrolyte body 72 via a spacer 80 so as to cover the measuring gas detecting electrode 74 while defining a measuring gas chamber 82, which permeate measuring gas to the measuring gas chamber 82 in a dispersed pattern. A shielding layer 84 is stacked on the diffusion resistance layer 78 on a surface opposite to the solid electrolyte body 72 and has a dense structure not to permeate gas.

Further, a chamber forming layer 86 is stacked on the other surface of the solid electrolyte body 72, on which the reference gas detecting electrode 76 is formed, via an intermediate bonding layer 90 formed in two layers 92, 94 in the same structure as that of the intermediate bonding layer 16 of the ceramic laminate body 10 of the first embodiment. The chamber forming layer 86 has one surface, facing the solid electrolyte body 72, which is formed with a recessed portion 86a that defines a reference gas chamber 88 in face with the reference gas detecting electrode 76.

In addition, a heater substrate 96, carrying thereon a plurality of heaters 98, is stacked on the other surface of the chamber forming layer 86.

Furthermore, the chamber forming layer 86 is stacked on the solid electrolyte body 72 via the intermediate bonding layer 90.

With the gas sensor element 70 shown in FIG. 10, the solid electrolyte body 72 corresponds to the first ceramic sheet 12 forming the ceramic laminate body 60 of the fifth embodiment shown in FIG. 9, and the chamber forming layer 86 corresponds to the second ceramic sheet 14 forming the ceramic laminate body 60 of the fifth embodiment shown in FIG. 9.

In addition, like the intermediate bonding layer 16 forming the ceramic laminate body 60 of the fifth embodiment shown in FIG. 9, the gas sensor element 70, shown in FIG. 10, includes the intermediate bonding layer 90 that comprises two unit intermediate layers 92, 94 with respective innermost end portions 92a, 94a being displaced from each other for the reasons set forth above.

The gas sensor element 70 has the other same structure as that of the ceramic laminate body 10 of the first embodiment shown in FIG. 1.

The gas sensor element 70, shown in FIG. 10, has an advantage with an increase in heat resistance while minimizing the occurrence of cracking or flaking in the ceramic sheets even under usage at high operating temperatures when installed on an exhaust system of an internal combustion engine with a view to detecting a specified gas concentration in exhaust gases.

Further, the gas sensor element 70 has the same other advantageous effects as those of the ceramic laminate body 10 of the first embodiment.

Seventh Embodiment

A gas sensor element of a seventh embodiment according to the present invention, incorporating the ceramic laminate structure 60 of the fifth embodiment shown in FIG. 9, is described with reference to FIGS. 11 to 13.

Figure 11:
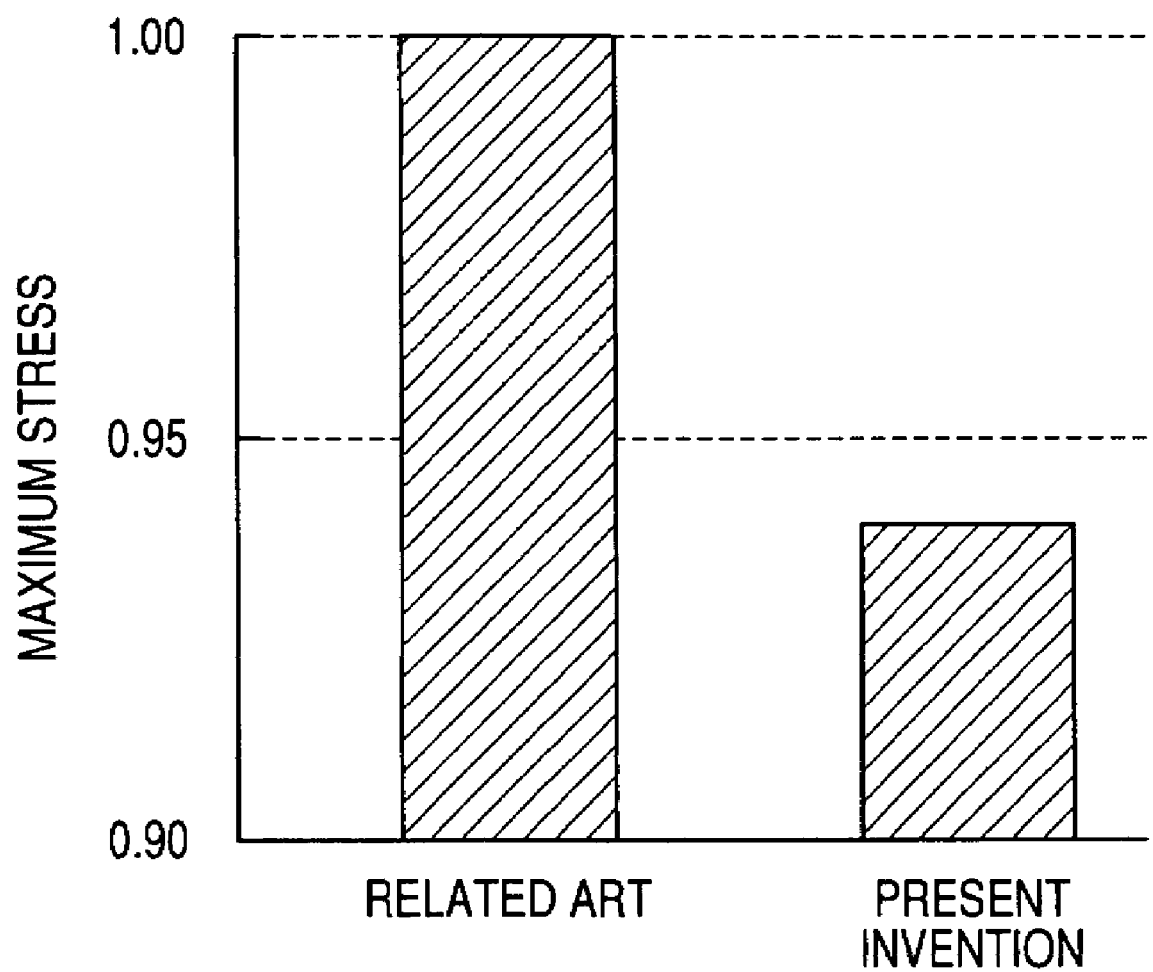
FIG. 11 is a graph showing measures results on the maximum stresses occurring in the related art ceramic laminate body and the laminate body implementing the present invention.

FIG. 11 is a graph showing the maximum stresses occurring in the related art ceramic laminate body and the ceramic laminate body of the present invention during a cooling state in respective firing steps.

Figure 12:
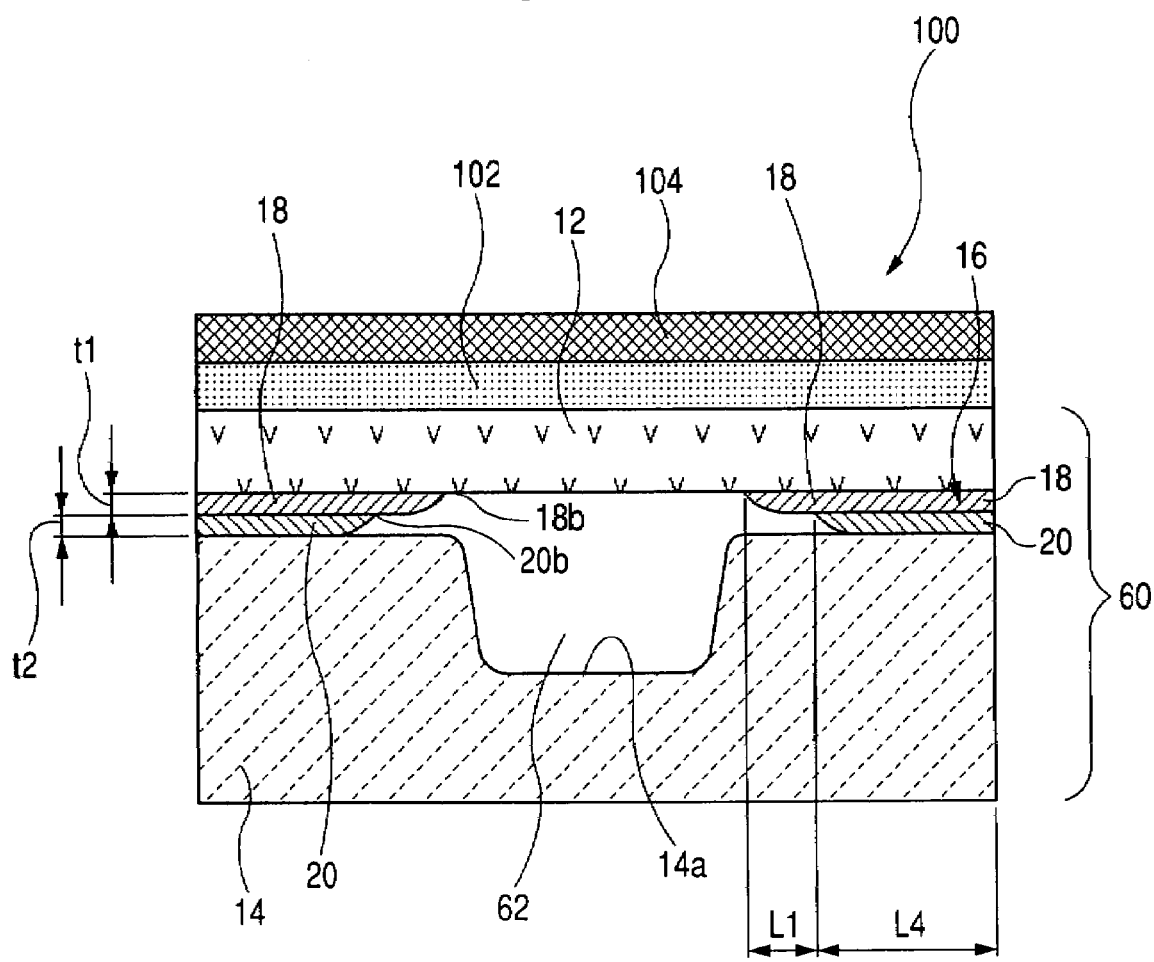
FIG. 12 is a cross sectional view showing a specimen used as a gas sensor element of a seventh embodiment according to the present invention.

FIG. 12 is a cross sectional view showing the gas sensor element 100 of the seventh embodiment acting as a specimen.

Figure 13:
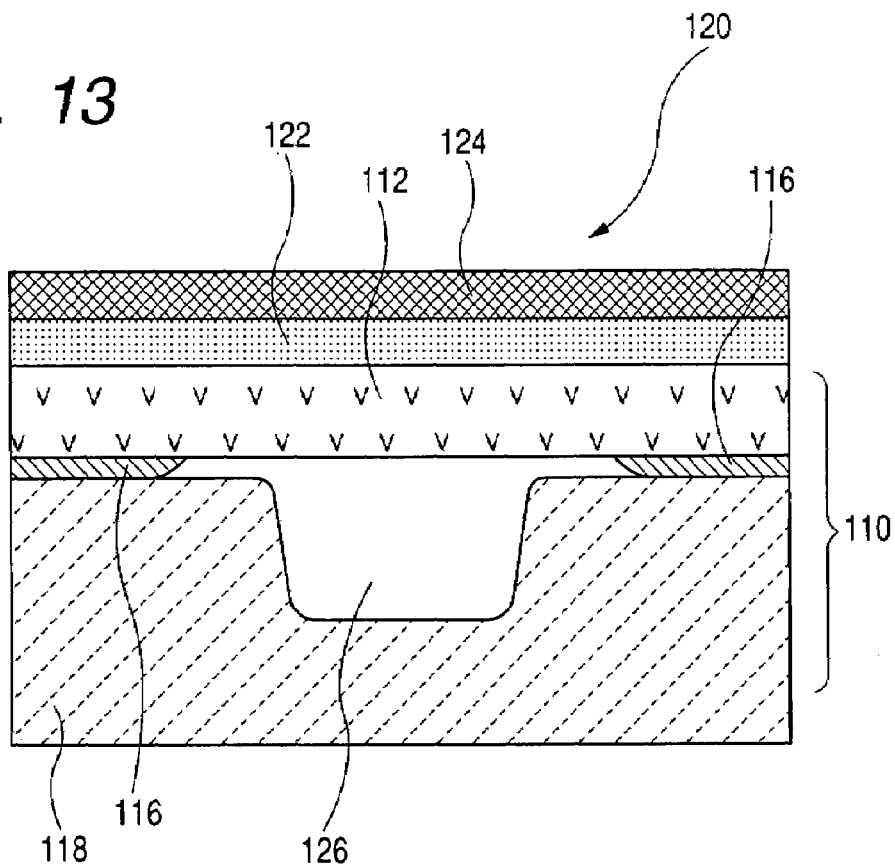
FIG. 13 is a cross sectional view showing another specimen used as a gas sensor element of the related art.

FIG. 13 is a cross sectional view showing a gas sensor element 120 as a comparison specimen.

As shown in FIG. 12, the gas sensor element 100 of the seventh embodiment was prepared as a specimen for test and comprised the ceramic laminate body 60 of the fifth embodiment shown in FIG. 9. The gas sensor element 100 of the present embodiment also included a diffusion resistance layer 102, stacked on the first ceramic sheet 12, and a shielding layer 104 stacked-on the diffusion resistance layer 102.

With the gas sensor element 100 of the present embodiment formed in such a structure, the unit intermediate layers 18, 20 had thicknesses t1, t2 each of which is selected to lie in a value of 15 cm. In addition, the innermost end portion 18b of the first unit intermediate layer 18 is displaced from the innermost end portion 20b of the second unit intermediate layer 20 by a displacement value of L1 that was selected to lie in a value of 0.2 mm.

Figure 16:
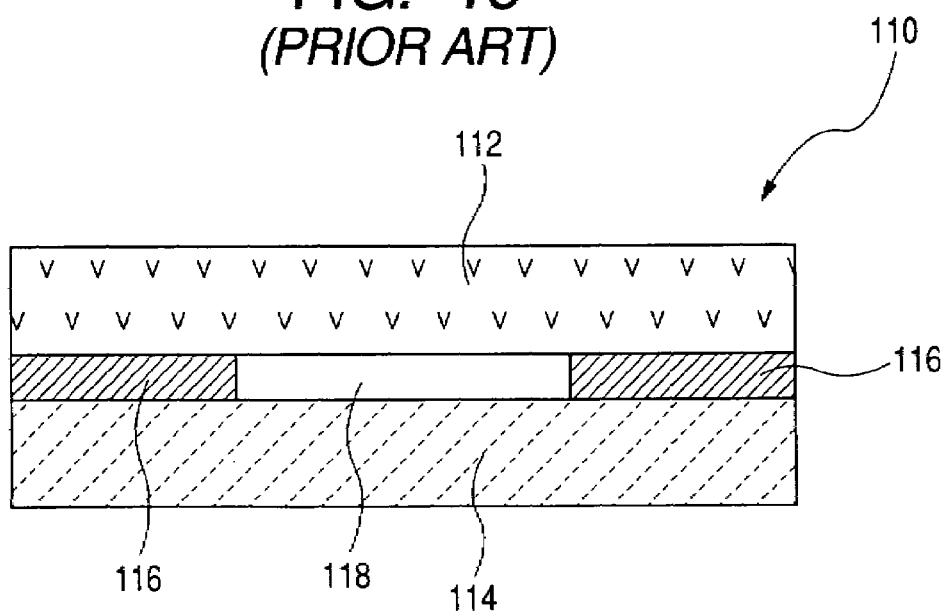
FIG. 16 is a cross sectional view showing a ceramic laminate of the related art.
Figure 17:
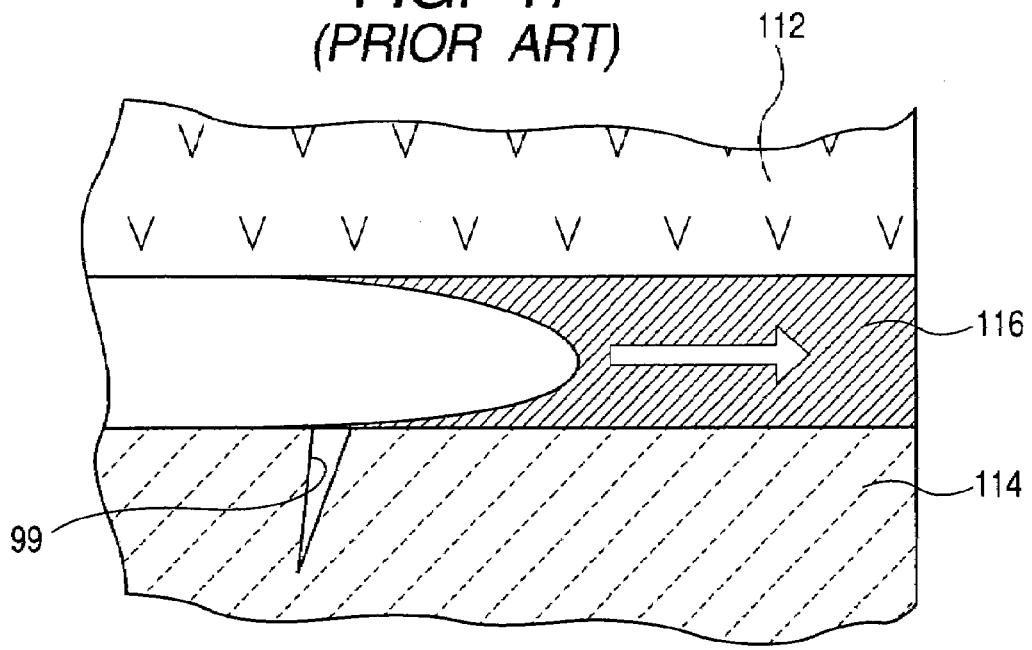
FIG. 17 is an illustrative view for illustrating a stress occurring in a boundary area between a ceramic green sheet and a bonding layer paste forming the ceramic laminate body of the related art shown in FIG. 16.
Figure 18:
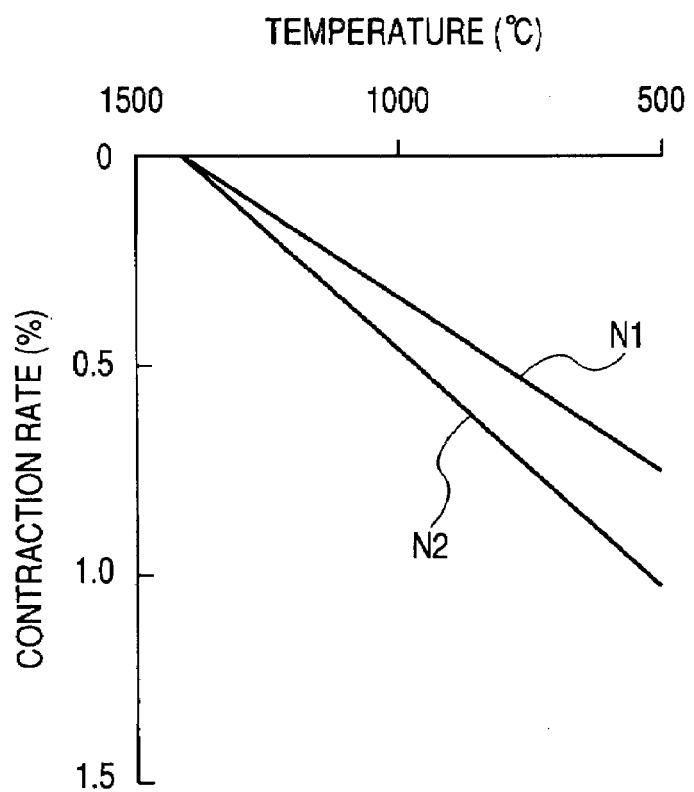
FIG. 18 is a graph showing a difference in contraction factors of two ceramic green sheets during cooling step.

In addition, the gas sensor element 120, shown in FIG. 13, was prepared as a specimen incorporating a structure of the ceramic laminate body 110 shown in FIG. 16 except for the provision of a closed hollow section 126. As shown in FIG. 13, the gas sensor element 120 includes, in addition to the ceramic laminate body 110, a diffusion resistance layer 122 stacked on the first ceramic sheet 112 acting as a solid electrolyte body and a shielding layer 124 stacked on the diffusion resistance layer 122. Here, the intermediate bonding layer 116 was selected to have a thickness of 15 μm.

Moreover, both of these gas sensor elements acting as the respective specimens have the other same structure as that of the gas sensor element 70 of the sixth embodiment shown in FIG. 10. However, with the structures shown in FIGS. 12 and 13, the illustrations of detecting electrodes and heater substrates are omitted.

These specimens were placed in firing steps for manufacturing the ceramic laminate bodies, respectively. To this end, these specimens were heated to the maximum temperatures for given time intervals and, then, cooled to a normal temperature. The maximum stresses acting on the first and second ceramic sheets 12, 14 (see FIG. 12) and the first and second ceramic sheets 112, 118 (see FIG. 13) during cooling steps were measured.

In the graph shown in FIG. 11, the maximum stress acting on the ceramic laminate body 120 of the related art was plotted to be "1" and the maximum stress appearing on the ceramic laminate body 100 implementing the present invention was plotted to have a value in contrast to the maximum stress acting on the ceramic laminate body 120 of the related art shown in FIG. 13.

Figure 14:
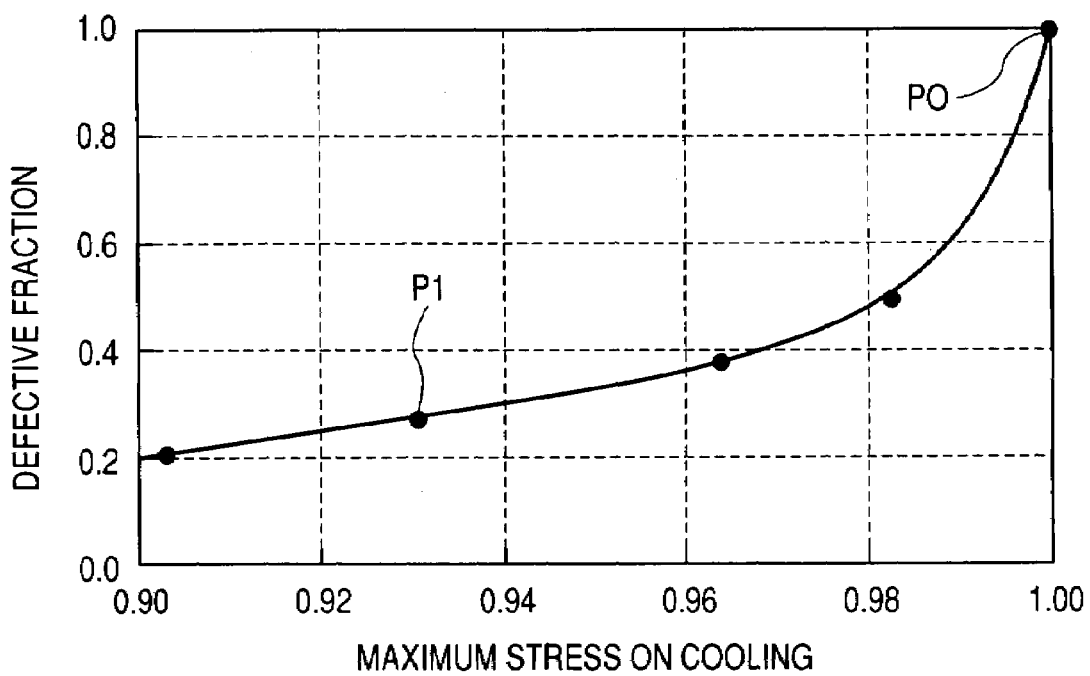
FIG. 14 is a graph showing the relationship between the maximum stress and defective fraction appearing in the gas sensor elements shown in FIGS. 12 and 13.

The relationships between the maximum stresses and defective fractions of the ceramic laminate bodies were checked, with the result being plotted in a graph shown in FIG. 14. In FIG. 14, the relationship between the maximum stress during cooling step and the defective fraction was plotted in contrast to the defective fraction, encountered with the ceramic laminate body of the related art, which was treated to be "1".

In the graph shown in FIG. 14, P0 designates data on the defective fraction of the related art ceramic laminate body and P1 designates data on the defective fraction of the ceramic laminate body implementing the present invention. In addition, the presence of a defect was determined when any of cracking or flaking encountered in the ceramic sheet 12 during cooling step.

As will be apparent from the graph of FIG. 14, it is turned out that the smaller the maximum stress occurring during cooling step, the lower will be the defective fraction. Thus, it will be understood that the ceramic laminate body implementing the present invention has an adequate effect of eliminating defective fraction.

Figure 15:
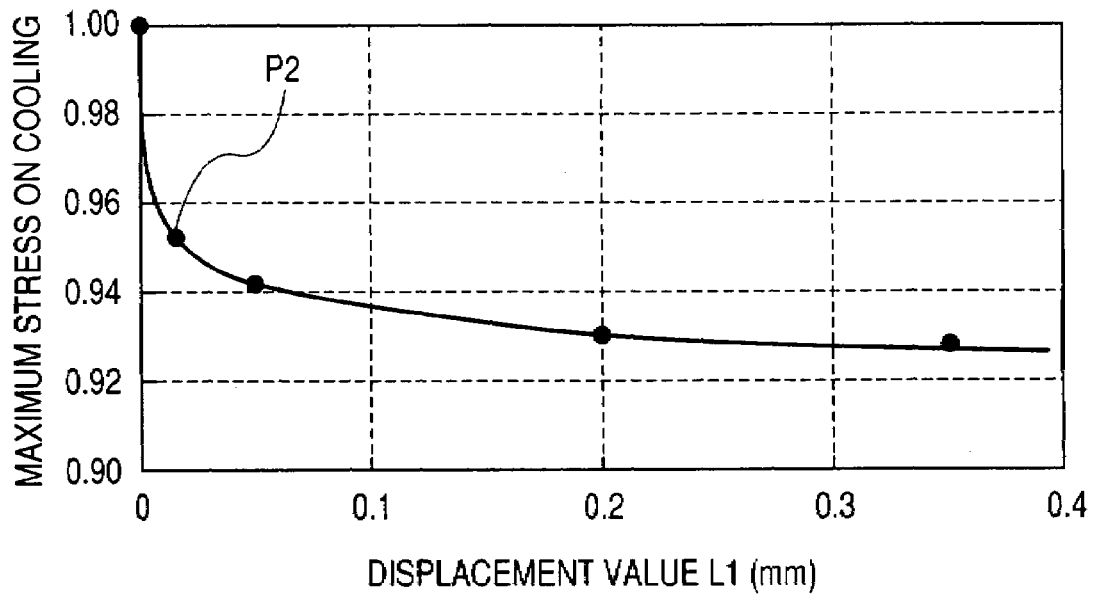
FIG. 15 is a graph showing the relationship between a displacement value L1 and the maximum stress appearing in the gas sensor elements shown in FIGS. 12 and 13.

FIG. 15 is a graph plotted with a test result on the relationship between a displacement value L1 between the innermost end portions 18b, 20b of the unit intermediate layers 18, 20 and the maximum stress occurring during cooling step.

Gas sensor elements each with the same structure as that of the ceramic laminate body 100 shown in FIG. 12 were used as specimens for evaluating ceramic laminate bodies implementing the present invention, with the gas sensor elements including the displacement value L1 altered upon changing a length of the first unit intermediate layer 18. The second intermediate layer 20 was formed in a fixed length L4 of 1.6 mm.

The evaluated result on the maximum stress occurring during cooling step is plotted in FIG. 15 in terms of the displacement value L1. In FIG. 15, P2 represents a measured point indicating a status where L1=t1.

As shown in FIG. 15, it is tuned out for the maximum stress to vary such as the greater the displacement value L1, the lower will be the maximum stress occurring during cooling step and the maximum stress occurring during cooling step can be remarkably reduced with the relationship established as $t \leq L1$. In addition, in the graph of FIG. 15, the maximum stress occurring in the first ceramic sheet 18 is plotted in terms of a proportion with respect to the maximum stress encountered with the related art structure and regarded to be "1".

While the specific embodiment of the present invention has been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalents thereof.

What is claimed is:

1. A gas sensor element comprising:
   a first ceramic sheet including a solid electrolyte body;
   a second ceramic sheet being made of material compositions different from those of the first ceramic sheet and including a chamber forming layer having one surface facing the solid electrolyte body and formed with a recessed portion defining a reference gas chamber;
   an intermediate bonding layer that bonds the first and second ceramic sheets to each other so as to form a closed hollow space between the first and second ceramic sheets and is formed only in an area between the solid electrolyte body and the chamber forming layer;
   wherein the intermediate bonding layer has a multilayer structure including first and second unit intermediate layers laminated on each other such that an innermost end portion of one of the first and second unit intermediate layers protrudes inward in the closed hollow space and is laterally offset from an innermost end portion of the other of the first and second unit intermediate layers, and
   wherein the first unit intermediate layer is formed on the solid electrolyte body and the second unit intermediate layer is formed on the chamber forming layer such that the first unit intermediate layer has the innermost end portion protruding toward the reference gas chamber to a further extent than the innermost end portion of the second unit intermediate layer, whereby the innermost end portions of the first and second unit intermediate layers define a stepped shape in cross section and the innermost end portions do not extend inward of a periphery of the reference gas chamber;
   a reference gas detecting electrode formed on one surface of the solid electrolyte body in face-to-face relation with the reference gas chamber;

a measuring gas detecting electrode formed on the other surface of the solid electrolyte body and exposed in a measuring gas chamber;

a diffusion resistance layer stacked on the other surface of the solid electrolyte body so as to define the measuring gas chamber in an area around the measuring gas detecting electrode and operative to permeate measuring gas to the measuring gas chamber; and a shielding layer laminated on the diffusion resistance layer.

2. The gas sensor element according to claim 1, wherein:
the first and second unit intermediate layers, forming the intermediate bonding layer, have a thickness ranging from 5 to 100 μm.

3. The gas sensor element according to claim 1, wherein:
the innermost end portion of the one of the first and second unit intermediate layers is displaced from the innermost end portion of the other of the first and second unit intermediate layers by a displacement value greater than a thickness of the one of the first and second unit intermediate layers.

4. The gas sensor element according to claim 1, wherein:
the one of the first and second unit intermediate layers is made of alumina in major proportions and the other of the first and second unit intermediate layers is made of zirconia in major proportions.

5. The gas sensor element according to claim 1, wherein:
the first and second unit intermediate layers have inward end portions, exposed to the closed hollow space, which have substantially arc-shaped configurations in cross section, respectively.

6. The gas sensor element according to claim 5, wherein:
the arc-shaped configurations of the first and second unit intermediate layers are aligned on the same orientations.

7. The gas sensor element according to claim 5, wherein:
the arc-shaped configurations of the first and second unit intermediate layers are aligned on the opposite orientations.

8. The gas sensor element according to claim 1, wherein:
the first and second unit intermediate layers have different degreasing contraction factors.

9. The gas sensor element according to claim 8, wherein:
the first unit intermediate layer comprises a hardened adhesive paste and the second unit intermediate layer comprises a hardened ceramic paste.

10. The gas sensor element according to claim 1, wherein:
the intermediate bonding layer further includes a third unit intermediate layer interposed between the second unit intermediate layer and the second ceramic sheet.

11. The gas sensor element according to claim 10, wherein:
the third unit intermediate layer has an innermost end portion protruding further inward to the closed hollow space than the innermost end portion of the second unit intermediate layer by a displacement value greater than a thickness of the third unit intermediate layer.

12. The gas sensor element according to claim 10, wherein:
the third unit intermediate layer has an innermost end portion exposed to the closed hollow space and is displaced outward from the innermost end portion of the second unit intermediate layer by a displacement value greater than a thickness of the third unit intermediate layer.

13. The gas sensor element according to claim 1, wherein:
the second ceramic sheet has a recessed portion to define a part of the closed hollow space.

14. The gas sensor element according to claim 1, wherein:
the innermost end portions of the first and second unit intermediate layers are displaced from each other by a displacement value expressed by $t \leq L1$ where "t" represents a thickness of one of the first and second unit intermediate layers and "L1" represents the displacement value between the innermost end portions of the first and second unit intermediate layers.

\* \* \* \* \*